United States Patent
Wang

(10) Patent No.: US 6,585,719 B2
(45) Date of Patent: Jul. 1, 2003

(54) LOW PROFILE METAL/POLYMER TUBES

(75) Inventor: Lixiao Wang, Long Lake, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 136 days.

(21) Appl. No.: 09/754,668

(22) Filed: Jan. 4, 2001

(65) Prior Publication Data

US 2002/0087142 A1 Jul. 4, 2002

(51) Int. Cl.[7] ............................................. A61M 25/00
(52) U.S. Cl. ...................................... 604/525; 604/534
(58) Field of Search ................................. 604/523, 529, 604/525, 526, 527, 528, 530, 531, 532, 533, 534, 535; 606/191, 192, 194

(56) References Cited

U.S. PATENT DOCUMENTS

| | | | |
|---|---|---|---|
| 2,211,975 A | 8/1940 | Hendrickson | 128/349 |
| 4,330,497 A | 5/1982 | Agdanowski | 264/150 |
| 4,569,347 A | 2/1986 | Frisbie | 128/344 |
| 4,657,024 A | 4/1987 | Coneys | 128/658 |
| 4,795,439 A | 1/1989 | Guest | 604/43 |
| 5,061,254 A | 10/1991 | Karakelle et al. | 604/265 |
| 5,102,401 A | 4/1992 | Lambert et al. | 604/264 |
| 5,163,431 A | 11/1992 | Griep | 128/658 |
| 5,329,923 A | 7/1994 | Lundquist | 128/642 |
| 5,381,782 A | 1/1995 | DeLaRama et al. | 128/4 |
| 5,454,787 A | 10/1995 | Lundquist | 604/95 |
| 5,470,322 A | 11/1995 | Horzewski et al. | 604/280 |
| 5,477,856 A | 12/1995 | Lundquist | 128/642 |
| 5,487,757 A * | 1/1996 | Truckai et al. | 604/264 |
| 5,507,751 A | 4/1996 | Goode et al. | 606/108 |
| 5,554,118 A * | 9/1996 | Jang | 604/102.02 |
| 5,569,218 A | 10/1996 | Berg | 604/282 |
| 5,573,520 A | 11/1996 | Schwartz et al. | 604/282 |
| 5,599,326 A | 2/1997 | Carter | 604/282 |
| 5,685,868 A | 11/1997 | Lundquist | 604/280 |
| 5,702,439 A | 12/1997 | Keith et al. | 604/96 |
| 5,741,429 A | 4/1998 | Donadio, III et al. | 216/8 |
| 5,921,956 A | 7/1999 | Grinberg et al. | 604/95 |
| 5,980,486 A | 11/1999 | Enger | 604/102 |
| 6,007,478 A | 12/1999 | Siess et al. | 600/16 |
| 6,071,273 A * | 6/2000 | Euteneuer et al. | 604/523 |
| 6,102,890 A | 8/2000 | Stivland et al. | 604/96 |
| 6,235,050 B1 * | 5/2001 | Quiachon et al. | 606/108 |
| 6,409,863 B1 * | 6/2002 | Williams et al. | 156/198 |

FOREIGN PATENT DOCUMENTS

| | | |
|---|---|---|
| DE | 4104092 | 2/1991 |
| JP | 8257128 | 10/1996 |

* cited by examiner

Primary Examiner—Edward K. Look
Assistant Examiner—John K Fristoe, Jr.
(74) Attorney, Agent, or Firm—Crompton, Seager & Tufte LLC

(57) ABSTRACT

The present invention relates generally to elongate support members, preferably for use with a catheter for performing medical procedures including percutaneous transluminal coronary angioplasty. An elongate support member comprising a proximal end and a distal end is disclosed. The proximal end of the elongate support member is formed to define a plurality of flanges. A linkage connects the flanges, and a lumen within the shaft is defined by connecting the flanges. The elongate support member comprises an improved catheter shaft design that maintains pushability, flexibility, and torquability while limiting kinking.

42 Claims, 4 Drawing Sheets

LOW PROFILE METAL/POLYMER TUBES

FIELD OF THE INVENTION

The present invention relates generally to catheters for performing medical procedures including percutaneous transluminal coronary angioplasty. More particularly, the present invention relates to balloon catheters with an improved proximal shaft design.

BACKGROUND OF THE INVENTION

The use of intravascular catheters has become an effective method for treating many types of vascular disease. In general, an intravascular catheter is inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular catheters include percutaneous transluminal angioplasty (PTA) and percutaneous transluminal coronary angioplasty (PTCA).

Intravascular catheters are commonly used in conjunction with a guidewire. A guidewire may be advanced through the patient's vasculature until it has reached a target location. Once in place, a catheter may be threaded onto the guidewire and urged distally until the distal end of the catheter reaches a target location.

Intravascular catheters adapted for use with a guidewire typically are classified as over-the-wire (OTW) or single operator exchange (SOE). An OTW catheter includes a guidewire lumen extending from the distal tip of the catheter to the proximal end of the catheter. When intravascular catheters are used, it is common for physicians to remove one catheter and exchange it for another. While exchanging catheters, the guidewire should preferably be held in place so as to keep its distal end near the target area. A portion of the guidewire is typically grasped by the physician in order to withdraw the first catheter while maintaining the distal end of the guidewire in the desired position. To properly anchor the guidewire, a portion of the guidewire should preferably be exposed at all times so it is available for the physician to grasp. In the case of an OTW catheter, the length of the guidewire extending beyond the patient's body should be longer than the catheter. Consequently, in many cases intravascular catheters are longer than 200 cm or require guidewire extensions to facilitate exchange, and there may be more than 200 cm of wire extending from the patient. Managing this length of wire during a catheter exchange procedure is awkward, and often requires more than one person. Additionally, contamination should be avoided by assuring that the guidewire is not dropped from the sterile field.

SOE catheters were developed in response to difficulties encountered when exchanging OTW catheters. Accordingly, SOE catheters have a relatively short guidewire lumen relative to the length of the catheter. Therefore, the length of guidewire extending beyond the body of the patient need only be slightly longer than the guidewire lumen of the catheter. The physician may anchor or hold the guidewire as the first catheter is removed from the body with the exchange occurring over the shorter guidewire lumen. The guidewire lumen of an SOE catheter typically includes a distal guidewire port disposed at the distal tip of the catheter and a proximal guidewire port disposed proximally of the distal end of the catheter.

When in use, intravascular catheters enter a patient's vasculature at a convenient location and then are urged to a target region. Once the distal portion of the catheter has entered the patient's vascular system, the physician may urge the distal tip forward by applying longitudinal forces to the proximal portion of the catheter. For the catheter to effectively communicate these longitudinal forces, it is desirable that the catheter have a high level of pushability and kink resistance particularly near the proximal end.

Frequently the path taken by a catheter through the vascular system is tortuous, requiring the catheter to change direction frequently. In some cases, it may even be necessary for the catheter to double back on itself. In order for the catheter to conform to a patient's tortuous vascular system, it is desirable that intravascular catheters be very flexible, particularly near the distal end.

Further, while advancing the catheter through the tortuous path of the patients vasculature, physicians often apply torsional forces to the proximal portion of the catheter to aid in steering the catheter. Torsional forces applied on the proximal end must translate to the distal end to aid in steering. It is therefore desirable that the proximal portion of an intravascular catheter have a relatively high level of torquability to facilitate steering.

The need for this combination of performance features is often addressed by manufacturing a catheter that has two or more discrete tubular members having different performance characteristics. For example, a relatively flexible distal section may be connected to a relatively rigid proximal section. When a catheter is formed from two or more discrete tubular members, it is often necessary to form a bond between the distal end of one tubular member and the proximal end of another tubular member.

An approach used to enhance pushability and torquability of intravascular catheters is to construct the proximal end from hypodermic tubing, or a "hypotube". While a hypotube can add significant pushability and torquability to an intravascular catheter due to its intrinsic strength and rigidity, it can kink if bent too sharply.

A need, therefore, exists for the manufacturing of SOE intravascular catheters to include shaft designs that maintain pushability, flexibility, and torquability while limiting kinking.

SUMMARY OF THE INVENTION

The present invention relates generally to catheters for performing medical procedures including percutaneous transluminal coronary angioplasty. More particularly, the present invention relates to catheters with improved proximal shaft designs. A preferred embodiment of the current invention includes an elongate support member with a proximal and distal end. The distal end of the elongate support member can be connected to the proximal end of a mid-region, the distal end of the mid-region connected to a distal region of a catheter shaft. Preferably, the distal region of the catheter shaft includes a therapeutic element such as an angioplasty balloon.

Multiple materials can be used to manufacture the elongate support member in different embodiments of the current invention. For example, the elongate support member can be manufactured from materials including, but not limited to thermoplastics, high performance engineering resins, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), metals, stainless steel, nickel alloys, nickel-titanium alloys, or other alloys.

In the preferred embodiment of the current invention, the elongate support member is formed so as to define a plurality of flanges. Forming the elongate support member can be accomplished by multiple methods including, but not limited to rolling a metallic sheet, cutting hollow cylindrical stock, modifying hypodermic tubing, or extrusion. After forming the elongate support member, it may resemble shapes that can be, but are not limited to, generally hemi-cylindrical, generally semi-cylindrical, generally rounded, partially rounded, and combinations thereof.

The flanges of the elongate support member can be connected to each other by a multiplicity of means according to differing embodiments of the current invention. According to the preferred embodiment of the current invention, a linkage is used to connect the flanges. The linkage includes a multiplicity of forms including, but not limited to a sheath, asymmetric sheath, and polymer cap.

The linkage can be manufactured from a multiplicity of materials including, but not limited to, thermoplastics, high performance engineering resins, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, and perfluoro(propyl vinyl ether) (PFA).

In a particular embodiment of the current invention, the linkage includes an asymmetric sheath. The sheath disposed about the elongate support member can be manufactured from materials including, but not limited to, polyether-ether ketone, polyimide, polyphenylene sulfide, and perfluoro (propyl vinyl ether). In differing embodiments of the current invention, in addition to a sheath, a linkage that directly connects the flanges may also be used. Further, combinations of different linkages may be used in multiple embodiments of the current invention. The sheath can be adhered to the elongate support member by a number of techniques including, but not limited to, heat shrinking.

Connection of the flanges defines a lumen extending from the proximal end of the catheter to the distal end of the elongate support member. The lumen may enable communication between the proximal and distal ends of the catheter. For example, the shaft may be used as an inflation lumen for angioplasty balloons. Additionally, the lumen of the formed elongate support member may be coated. For example, the elongate support member may be coated with polytetrafluoroethylene (PTFE).

In an exemplary embodiment of the current invention, the flanges are connected using an over wire extrusion method. According to this embodiment of the current invention, the linkage connecting the flanges is attached to the elongate support member by extrusion. For example, a wire is placed within an elongate support member comprising a plurality of flanges and extruded so as to attach a linkage disposed over the elongate support member. In an alternative embodiment of the current invention, the flanges are connected by adhesives. The adhesives include, but are not limited to, epoxy or polyurethane.

An additional embodiment of the current invention comprises the use of a polymer cap that is adhered with adhesive or thermal binding with a primer to connect the flanges. Preferably, the polymer cap is attached by first attaching a coupling agent or primer to the flanges. The coupling agent may allow easier attachment of the polymer cap to the flanges. Alternatively, the polymer cap may be attached to the flanges by thermal binding.

DETAILED DESCRIPTION OF THE PREFERRED EMBODIMENTS

Figure 1:
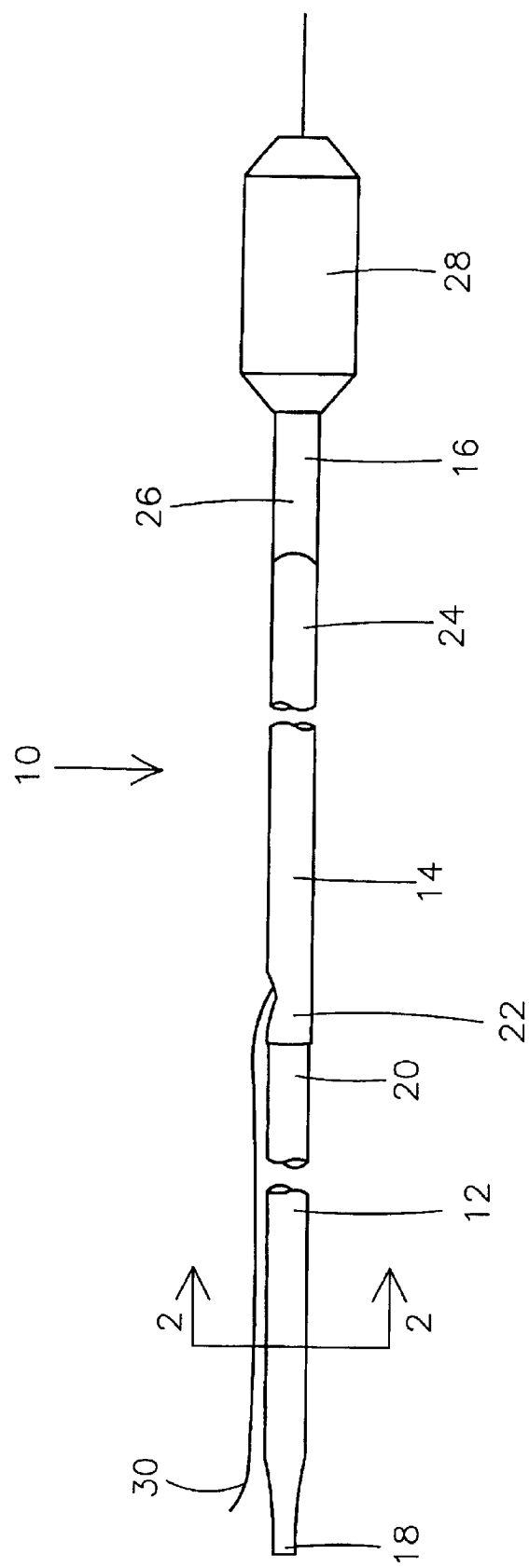
FIG. 1 is a plan view of a catheter in accordance with an exemplary embodiment of the current invention.

Referring now to the drawings wherein like reference numerals indicate like elements throughout the several views, FIG. 1 is a plan view of a catheter in accordance with an exemplary embodiment of the current invention. According to the preferred embodiment of the current invention, a catheter 10 comprises an elongate support member 12, a mid-region 14, and a distal region 16. Mid-region 14 further comprises a proximal end 22 and a distal end 24. Elongate support member 12 includes a proximal end 18 and a distal end 20. Distal end 20 of elongate support member 12 connects with a proximal end 22 of mid-region 14. A distal end 24 of mid-region 14 connects with a proximal end 26 of distal region 16 of catheter 10. Distal region 16 may include multiple therapeutics including, but not limited to, an angioplasty balloon 28. The catheter further comprises a guidewire 30 for use in guiding the catheter to an area of interest.

The catheter may include both single operator exchange (SOE) or over the wire (OTW) catheters known to those skilled in the art. Further, multiple embodiments of the current invention utilize the improved elongate support member in catheters and other devices as disclosed in accordance with the current invention.

Figure 2:
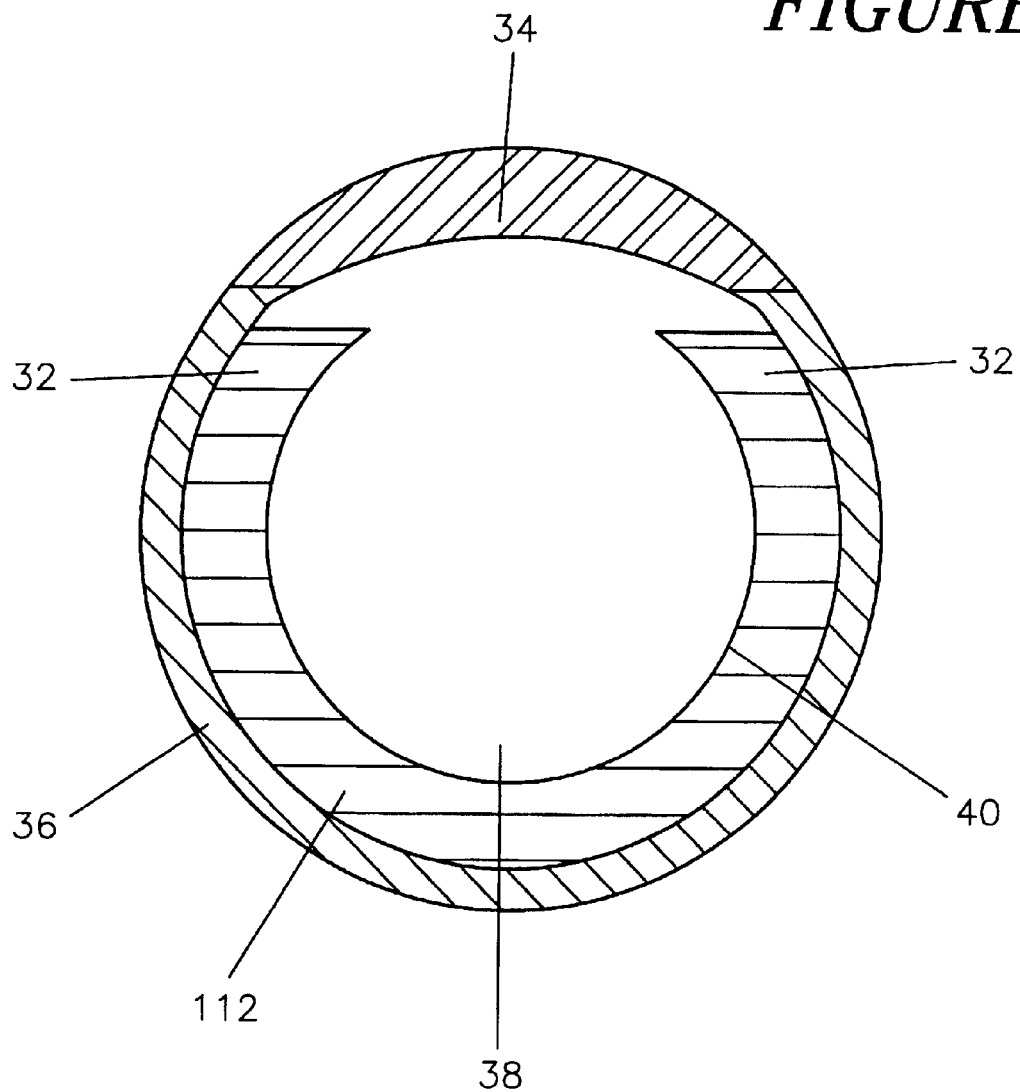
FIG. 2 is a cross-sectional view of the elongate support member wherein the linkage includes an asymmetric sheath.

FIG. 2 is a cross-sectional view of the elongate support member wherein the linkage includes an asymmetric sheath. The asymmetric sheath connects the flanges 32 according to the preferred embodiment of the current invention.

An elongate support member 112 is formed to define a plurality of flanges 32. Elongate support member 112 may be formed by a multiplicity of methods. For example, the elongate support member may be formed by rolling a metallic sheet into shape that is preferably generally hemi-cylindrical, generally semi-cylindrical, generally rounded, partially rounded, or combinations thereof. These shapes define a plurality of flanges for multiple embodiments of the current invention.

Flanges 32 are connected by a linkage 34. Linkage 34, as shown in FIG. 2, further comprises an asymmetric sheath 36. Linkage 34 may be manufactured from a multiplicity of materials including, but not limited to, thermoplastics, high performance engineering resins, polymers, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, and perfluoro(propyl vinyl ether) (PFA). In an alternative embodiment of the current invention, the flanges are connected by adhesives. The adhesives include, but are not limited to, epoxy or polyurethane.

Sheath 36 may be attached to the elongate support member by a multiplicity of methods including, but not limited to, heat shrinking. When using heat shrinking, according to the preferred embodiment of the current invention, the sheath is disposed about the elongate support member and attached to it. The sheath is then adhered to the elongate support member using heat shrinking methods known in the art.

Connection of flanges 32 defines a lumen 38. Lumen 38 may enable communication between the proximal and distal ends of the catheter. For example, lumen 38 may be used as an inflation lumen for angioplasty balloons.

Preferably, the inner surface of elongate support member 112 is coated with a coating 40. For example, the elongate support member may be coated with polytetrafluoroethylene (PTFE). Coating 40 preferably forms a lower friction surface. In an exemplary embodiment of the current invention, the coated surface may provide a means for releasing a wire used to maintain the lumen within the elongate support member, when the elongate support member is formed using over wire extrusion.

Figure 3:
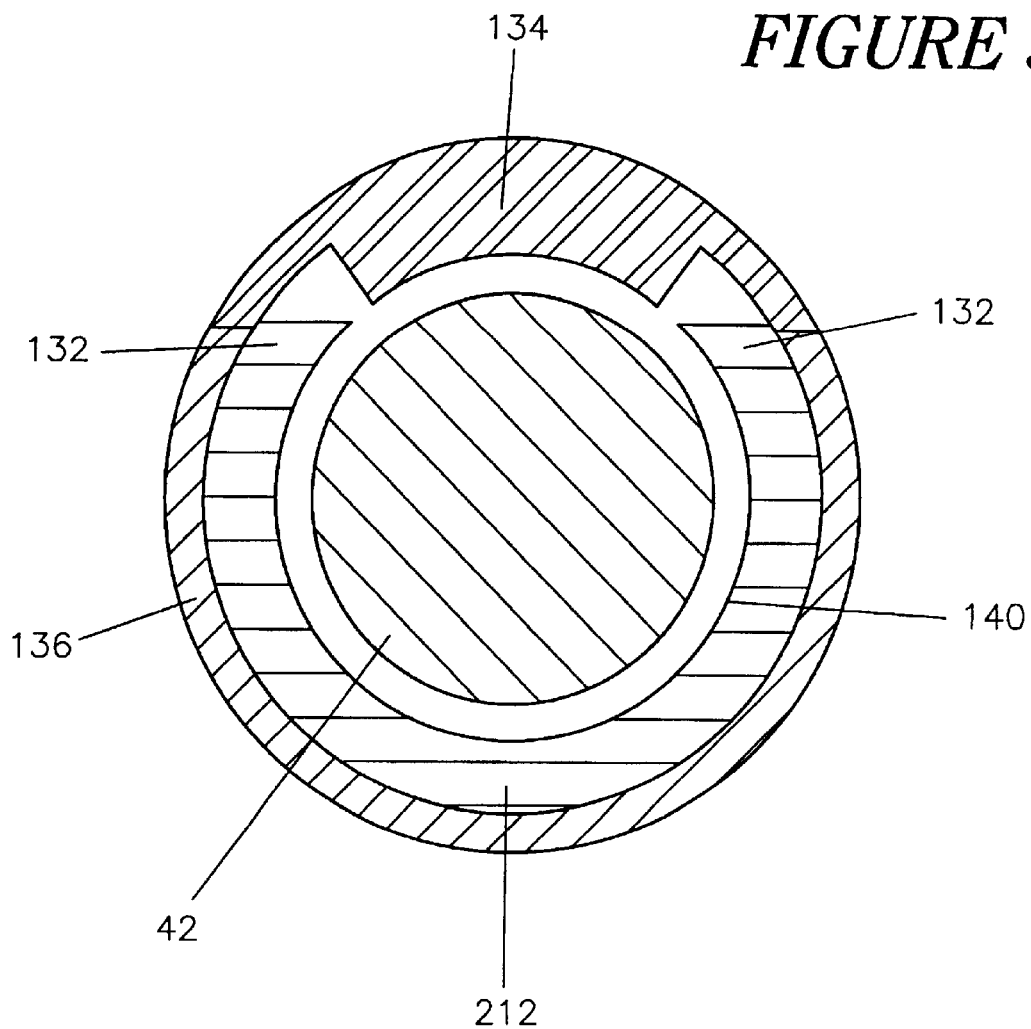
FIG. 3 is an alternate cross-sectional view of the elongate support member wherein the linkage connects the flanges through the process of over wire extrusion.

FIG. 3 is an alternate cross-sectional view of the elongate support member wherein a linkage that connects the flanges is attached to the elongate support member by over wire extrusion. Over wire extrusion, familiar to those skilled in the art, can be used to manufacture the proximal end of a catheter according to multiple embodiments of the current invention. Elongate support member 212 is formed to define a plurality of flanges 132. Forming elongate support member 212 may occur as discussed above.

Flanges 132 can be connected by linkage 134. Linkage 134 may further comprise sheath 136. Linkage 134 may be manufactured from a multiplicity of materials including, but not limited to, thermoplastics, high performance engineering resins, polymers, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, and perfluoro(propyl vinyl ether) (PFA).

Preferably, linkage 134 is attached to elongate support member 212 by over wire extrusion, wherein a wire 42 is placed along an inner surface of elongate support member 212. Extrusion results in the attachment of linkage 134 to elongate support member 212, connecting flanges 132. Additionally, linkage 134 may further comprise sheath 136, including an asymmetric sheath.

Wire 42, preferably, is placed along an inner surface of elongate support member 212. Wire 42 can be used to form a lumen within elongate support member 212. For example, wire 42 can be places along an inner surface of elongate support member 212 prior to extrusion. Next, elongate support member 212 is subjected to extrusion, wherein linkage 134 connects flanges 132. Wire 42, prevents linkage 134 from entering the lumen defined by connection of flanges 132. Following extrusion, the lumen can be recovered by removing wire 42.

The inner surface of elongate support member 212 may be coated with coating 140. For example, elongate support member 212 may be coated with polytetrafluoroethylene (PTFE). Coating 140 preferably forms a lower friction surface. In an exemplary embodiment of the current invention, the coated surface may provide a means for releasing a wire used to maintain the lumen within the elongate support member, when the elongate support member is formed using over wire extrusion. One skilled in the art would be familiar with the use of coating an elongate support member appropriate for multiple embodiments of the current invention.

Figure 4:
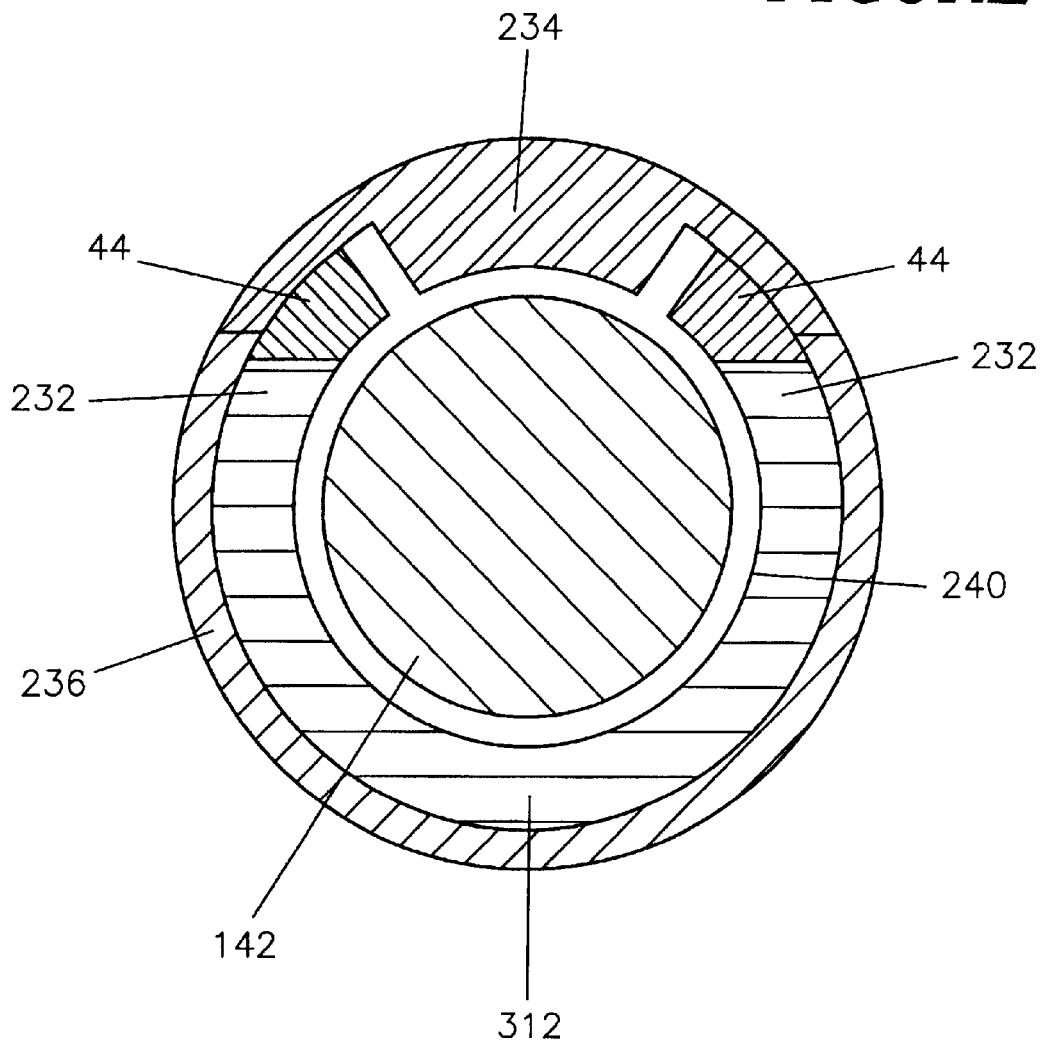
FIG. 4 is an alternate cross-sectional view of the elongate support member wherein the linkage includes a polymer cap.

FIG. 4 is an alternate cross-sectional view of the elongate support member wherein the linkage includes a polymer cap. The polymer cap may be attached to the elongate support member by a multiplicity of methods including, but not limited to, thermal binding, thermal binding using a primer or coupling agent, and using adhesives.

Elongate support member 312 is formed to define a plurality of flanges 232. Elongate support member 312 may be formed by a multiplicity of methods, as described above. For example, the elongate support member may be formed by rolling a metallic sheet, cutting hollow cylindrical stock, modifying hypodermic tubing, or extrusion. After forming the elongate support member, it may resemble shapes that can be, but are not limited to, generally hemi-cylindrical, generally semi-cylindrical, generally rounded, partially rounded, and combinations thereof. These shapes define a plurality of flanges for multiple embodiments of the current invention.

Flanges 232 are connected by polymer cap linkage 234. Additionally, the linkage may further comprise sheath 236. The polymer cap linkage may be manufactured from a multiplicity of materials including, but not limited to, polymers, thermoplastics, high performance engineering resins, polymers, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, and perfluoro(propyl vinyl ether) (PFA). In an alternative embodiment of the current invention, the flanges are connected by adhesives. The adhesives include, but are not limited to, epoxy or polyurethane. In an exemplary embodiment, connection of flanges 232 is accomplished by first attaching a coupling agent or primer 44 to flanges 232.

The coupling agent then can enable the attachment of polymer cap 234 to connect flanges 232. One skilled in the art would be familiar with attaching a polymer cap using differing coupling agents or primers according to multiple embodiments of the current invention. Further, the polymer cap may be attached without the use of a coupling agent or primer.

The inner surface of elongate support member 312 may be coated with a coating 240. For example, the elongate support member may be coated with polytetrafluoroethylene (PTFE). The coating preferably forms a lower friction surface. In an exemplary embodiment of the current invention, the coated surface may provide a means for releasing a wire used to maintain the lumen within the elongate support member, when the elongate support member is formed using over wire extrusion. Alternate embodiments of the current invention can be conceived that combine over wire extrusion with the attachment of a polymer cap.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An elongate support member for use with a catheter, said elongate support member comprising:
   a metallic object;
   the metallic object formed to define a plurality of flanges, a proximal end, and a distal end;
   a linkage connecting the flanges, said linkage including a tubular sheath disposed about the elongate support member; and
   a lumen defined by connecting the flanges.

2. The elongate support member in accordance with claim 1, wherein the elongate support member is generally hemi-cylindrical.

3. The elongate support member in accordance with claim 1, wherein the elongate support member is generally semi-cylindrical.

4. The elongate support member in accordance with claim 1, wherein the elongate support member is generally rounded.

5. The elongate support member in accordance with claim 1, wherein the elongate support member is partially round.

6. The elongate support member in accordance with claim 1, wherein the linkage includes adhesives.

7. The elongate support member in accordance with claim 1, wherein the linkage includes epoxy.

8. The elongate support member in accordance with claim 1, wherein the linkage includes a polymer.

9. The elongate support member in accordance with claim 8, wherein the polymer is selected from a list consisting of thermoplastics, high performance engineering resins, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, and perfluoro(propyl vinyl ether) (PFA).

10. The elongate support member in accordance with claim 1, wherein the linkage includes a polymer cap.

11. The elongate support member in accordance with claim 1, wherein said catheter includes a guidewire port.

12. The elongate support member in accordance with claim 1, wherein a balloon is attached to said catheter.

13. A method of manufacturing a catheter shaft comprising an elongate support member with a proximal and distal end, the distal end of the elongate support member connected to a mid-region comprising a proximal and distal end, the distal end of the mid-region connected to a distal region, comprising the steps of:

forming the elongate support member to define a plurality of flanges;

connecting the flanges with a linkage; and disposing a sheath about the elongate support member.

14. The method in accordance with claim 13, wherein the step of forming the elongate support member to define a plurality of flanges includes modifying hypodermic tubing.

15. The method in accordance with claim 13, wherein the step of forming the elongate support member to define a plurality of flanges includes rolling a metallic sheet.

16. The method in accordance with claim 13, wherein the linkage includes adhesives.

17. The method in accordance with claim 13, wherein the linkage includes epoxy.

18. The method in accordance with claim 13, wherein the linkage includes a polymer.

19. The method in accordance with claim 18, wherein the polymer is selected from a list consisting of thermoplastics, high performance engineering resins, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, and perfluoro(propyl vinyl ether) (PFA).

20. The method in accordance with claim 13, wherein the linkage includes a polymer cap.

21. The method in accordance with claim 13, wherein the step of connecting the flanges with a linkage further comprises thermal binding.

22. The method in accordance with claim 13, wherein the step of disposing a sheath about the elongate support member further comprises heat shrinking.

23. The method in accordance with claim 13, wherein the step of disposing a sheath about the elongate support member includes disposing an asymmetric sheath about the elongate support member.

24. An intravascular catheter, comprising:

an elongate support member having a proximal end, a distal end, and a lumen therethrough, said elongate support member defining a proximal shaft region of the catheter;

a mid-region connected at a proximal end to the distal end of the elongate support member, and at a distal end to a distal region of the catheter;

wherein the elongate support member is formed of a plurality of flanges, and a linkage connecting said flanges, wherein the linkage includes a sheath disposed about the elongate support member.

25. The catheter in accordance with claim 24, wherein the flanges are formed by rolling a metallic sheet.

26. The catheter in accordance with claim 24, wherein the elongate support member is generally hemi-cylindrical.

27. The catheter in accordance with claim 24, wherein the elongate support member is generally semi-cylindrical.

28. The catheter in accordance with claim 24, wherein the elongate support member is generally rounded.

29. The catheter in accordance with claim 24, wherein the elongate support member is partially round.

30. The catheter in accordance with claim 24, wherein the elongate support member is constructed of a polymer.

31. The catheter in accordance with claim 24, wherein the elongate support member is constructed of metal.

32. The catheter in accordance with claim 24, wherein the elongate support member is constructed of stainless steel.

33. The catheter in accordance with claim 24, wherein the elongate support member is constructed of nickel alloy.

34. The catheter in accordance with claim 24, wherein the elongate support member is constructed of nickel-titanium alloy.

35. The catheter in accordance with claim 24, wherein the linkage includes an asymmetric sheath disposed about the elongate support member.

36. The catheter in accordance with claim 24, wherein the linkage includes adhesives.

37. The catheter in accordance with claim 24, wherein the linkage includes epoxy.

38. The catheter in accordance with claim 24, wherein the linkage includes a polymer.

39. The catheter in accordance with claim 38, wherein the polymer is selected from a list consisting of thermoplastics, high performance engineering resins, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, and perfluoro(propyl vinyl ether) (PFA).

40. The catheter in accordance with claim 24, wherein the linkage includes a polymer cap.

41. The catheter in accordance with claim 24, wherein the mid-region of said catheter includes a guidewire port.

42. The catheter in accordance with claim 24, wherein a balloon is attached to the distal region of said catheter.

* * * * *